(12) United States Patent
Zemtsov

(10) Patent No.: US 9,566,306 B2
(45) Date of Patent: *Feb. 14, 2017

(54) FORMULATIONS AND METHODS FOR TREATMENT OF WOUNDS AND INFLAMMATORY SKIN CONDITIONS

(71) Applicant: Zemtsov Enterprises, LLC, Yorktown, IN (US)

(72) Inventor: Alexander Zemtsov, Yorktown, IN (US)

(73) Assignee: Zemtsov Enterprises, LLC, Yorktown, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/394,641

(22) PCT Filed: Mar. 17, 2013

(86) PCT No.: PCT/US2013/032728
§ 371 (c)(1),
(2) Date: Oct. 15, 2014

(87) PCT Pub. No.: WO2013/158319
PCT Pub. Date: Oct. 24, 2013

(65) Prior Publication Data
US 2015/0072996 A1    Mar. 12, 2015

Related U.S. Application Data

(60) Provisional application No. 61/624,725, filed on Apr. 12, 2012, provisional application No. 61/725,761, filed on Nov. 13, 2012.

(51) Int. Cl.
| | | |
|---|---|---|
| *A61K 31/4965* | (2006.01) | |
| *A61K 35/57* | (2015.01) | |
| *A61K 47/44* | (2006.01) | |
| *A61K 9/00* | (2006.01) | |
| *A61K 45/06* | (2006.01) | |
| *A61K 31/573* | (2006.01) | |
| *A61K 9/06* | (2006.01) | |
| *A61K 31/197* | (2006.01) | |
| *A61K 31/20* | (2006.01) | |
| *A61K 31/201* | (2006.01) | |
| *A61K 31/202* | (2006.01) | |
| *A61K 31/495* | (2006.01) | |
| *A61K 47/10* | (2006.01) | |
| *A61K 47/14* | (2006.01) | |
| *A61K 31/57* | (2006.01) | |
| *A61K 31/203* | (2006.01) | |

(52) U.S. Cl.
CPC .............. *A61K 35/57* (2013.01); *A61K 9/0014* (2013.01); *A61K 9/06* (2013.01); *A61K 31/197* (2013.01); *A61K 31/20* (2013.01); *A61K 31/201* (2013.01); *A61K 31/202* (2013.01); *A61K 31/203* (2013.01); *A61K 31/495* (2013.01); *A61K 31/57* (2013.01); *A61K 31/573* (2013.01); *A61K 45/06* (2013.01); *A61K 47/10* (2013.01); *A61K 47/14* (2013.01); *A61K 47/44* (2013.01)

(58) Field of Classification Search
None
See application file for complete search history.

(56) References Cited

U.S. PATENT DOCUMENTS

| 4,772,591 | A | 9/1988 | Meisner |
| 5,431,924 | A | 7/1995 | Ghosh et al. |
| 5,744,128 | A | 4/1998 | Holick |
| 5,958,384 | A | 9/1999 | Holick |
| 6,103,246 | A | 8/2000 | Tisdale et al. |
| 6,342,208 | B1 | 1/2002 | Hyldgaard et al. |
| 6,667,026 | B1 | 12/2003 | Goldman et al. |
| 6,720,001 | B2 | 4/2004 | Chen et al. |

(Continued)

FOREIGN PATENT DOCUMENTS

| EP | 1637135 A1 | 3/2006 |
| WO | 92/08470 | 5/1992 |

(Continued)

OTHER PUBLICATIONS

International Search Report and Written Opinion for PCT/US13/32728 dated Jun. 17, 2013, 15 Pages.

(Continued)

*Primary Examiner* — Jean Cornet
(74) *Attorney, Agent, or Firm* — Reichel Stohry LLP; Mark C. Reichel; Natalie J. Dean

(57) ABSTRACT

The disclosure of the present application includes topically administrable compositions and methods for treating wounds and inflammatory conditions of the skin in mammals. In an exemplary embodiment, the composition includes a therapeutic amount of antihistamine selected from the group consisting of a non-sedating antihistamine, a physiologically acceptable acid of a non-sedating antihistamine, a salt of a non-sedating antihistamine, an amide of a non-sedating antihistamine, and a combination of two or more of these; a therapeutic amount of creatine; a therapeutic amount of creatinine; and emu oil product selected from the group consisting of emu oil, a biologically active fraction of emu oil, and a combination of these. The combination of non-sedating antihistamine, creatine, and creatinine with emu oil has been found to produce a synergistic effect that is more effective in the treatment of skin wounds than the compounds used separately.

10 Claims, 1 Drawing Sheet

(56) References Cited

U.S. PATENT DOCUMENTS

| | | | |
|---|---|---|---|
| 6,790,847 B2 * | 9/2004 | Walch | A61K 9/0014 424/78.05 |
| 6,806,213 B2 * | 10/2004 | Brooks | D04H 1/42 15/209.1 |
| 7,048,950 B2 * | 5/2006 | Farmer | A61K 9/0014 424/522 |
| 7,316,820 B2 | 1/2008 | Jordan | |
| 8,114,385 B2 | 2/2012 | Tamarkin et al. | |
| 8,128,947 B2 | 3/2012 | Jones et al. | |
| 8,232,317 B2 | 7/2012 | Gan et al. | |
| 2003/0212078 A1 | 11/2003 | Klein | |
| 2004/0132743 A1 | 7/2004 | Reddy et al. | |
| 2004/0185115 A1 | 9/2004 | Pearson et al. | |
| 2004/0198743 A1 | 10/2004 | Hey et al. | |
| 2004/0208860 A1 | 10/2004 | Farmer | |
| 2004/0241197 A1 * | 12/2004 | Biergiesser | A61K 8/43 424/401 |
| 2004/0266787 A1 | 12/2004 | Reddy et al. | |
| 2005/0176732 A1 | 8/2005 | Cossement et al. | |
| 2005/0182070 A1 | 8/2005 | Gobert | |
| 2005/0238597 A1 | 10/2005 | McCook et al. | |
| 2007/0009607 A1 | 1/2007 | Jones | |
| 2007/0079447 A1 | 4/2007 | Kroepke et al. | |
| 2007/0207222 A1 | 9/2007 | Yu et al. | |
| 2008/0025929 A1 | 1/2008 | Burton et al. | |
| 2008/0031833 A1 | 2/2008 | Oblong et al. | |
| 2008/0124381 A1 | 5/2008 | Barnhart et al. | |
| 2008/0208179 A1 | 8/2008 | Chan et al. | |
| 2008/0255103 A1 | 10/2008 | Aslam et al. | |
| 2009/0053290 A1 | 2/2009 | Sand et al. | |
| 2009/0068128 A1 | 3/2009 | Waddington | |
| 2009/0176792 A1 | 7/2009 | Gant et al. | |
| 2009/0304812 A1 | 12/2009 | Staniforth et al. | |
| 2010/0008868 A1 | 1/2010 | Dugger | |
| 2010/0055161 A1 | 3/2010 | Ahn | |
| 2010/0063008 A1 | 3/2010 | Matteliano et al. | |
| 2010/0203122 A1 | 8/2010 | Weyer et al. | |
| 2010/0221194 A1 | 9/2010 | Loupenok | |
| 2011/0104159 A1 | 5/2011 | Rohrs et al. | |
| 2012/0027876 A1 | 2/2012 | Ford | |
| 2012/0045486 A1 | 2/2012 | Bravo Cordero et al. | |
| 2012/0064011 A1 | 3/2012 | Schumann | |
| 2012/0100183 A1 | 4/2012 | Schlessinger et al. | |
| 2012/0183588 A1 | 7/2012 | Supamahitorn et al. | |
| 2012/0315235 A1 | 12/2012 | Weisenfluh | |

FOREIGN PATENT DOCUMENTS

| | | |
|---|---|---|
| WO | 96/34596 | 11/1996 |
| WO | 0113956 A2 | 3/2001 |
| WO | 01/87236 | 11/2001 |

OTHER PUBLICATIONS

International Preliminary Report on Patentability for PCT/US13/32728 dates Apr. 14, 2014, 19 Pages.

Zemtsov, A, A Novel Vehicle Formulation for Treatment of Inflammatory Skin Diseases, Journal of Cosmetics, Dermatological Sciences and Applications, Jan. 1, 2013, pp. 18-21, vol. 3, No. 1.

Extended European Search Report, EP 13778264.5, Feb. 11, 2015, 8 pages.

Extended European Search Report, EP 13777719.9, Feb. 11, 2015, 9 pages.

Extended European Search Report, EP 13777761.1, Feb. 11, 2015, 8 pages.

\* cited by examiner

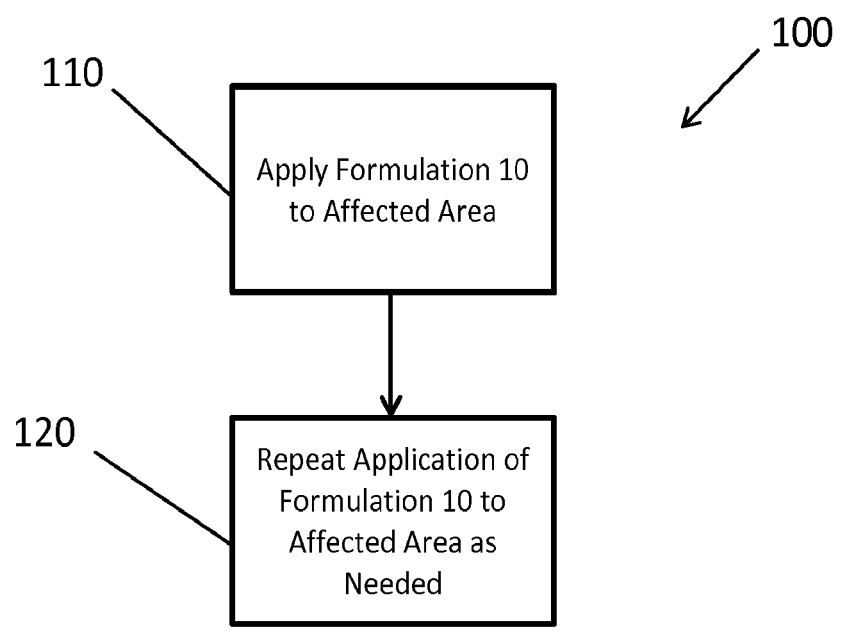

FORMULATIONS AND METHODS FOR TREATMENT OF WOUNDS AND INFLAMMATORY SKIN CONDITIONS

PRIORITY

The present application is a U.S. National Phase of International PCT Application No. PCT/US13/32728 filed on Mar. 17, 2013, and is also related to, and claims the priority benefit of, U.S. Provisional Patent Application Ser. No. 61/624,725, filed Apr. 16, 2012, and 61/725,761, filed Nov. 13, 2012, each of which is hereby incorporated by reference in their entirety into this disclosure.

BACKGROUND

The emu (*Dromiceius novae-hollandiae*) is the second largest member of the group of flightless birds and is indigenous to Australia. Emus can be raised like ordinary farm animals and used for their valuable products, which include very low fat meat, supple leather hides, decorative and nutritional eggs, and rich oil. Emu oil may be extracted or rendered from the body fat of the emu and is known to contain triglyceride esters of long-chain saturated and unsaturated fatty acids, including oleic acid, linoleic acid, palmitic acid, and stearic acid.

Atopic dermatitis and other forms of eczema are inflammatory, pruritic (i.e., itchy) skin diseases that affect between 10 and 20 percent of the United States (U.S.) population, causing considerable morbidity, poor quality of life, and high medical costs for both the patient and society. Topically administered glucocorticoids are a main form of therapy; however, prolonged use of topical glucocorticoids is associated with skin thinning, permanent stretch marks, dermal atrophy, rebound effects, tachyphylaxis, and potential systemic absorption, which can cause numerous systemic side effects. Topical calcineurin inhibitors (e.g., Elidel® and Protopic® creams and ointments) are effective but are infrequently used as a result of FDA-required "black box" warnings concerning a potential increase in systemic malignancies in patients using these topical preparations.

Psoriasis is also a chronic pruritic inflammatory skin disease affecting 2% of the U.S. population. Inflammation and tumor necrosis factor-alpha ("TNF-alpha") are of crucial importance in the pathogenesis of psoriasis and its treatment. Based on the severity of the disease presentation, topical glucocorticoids, and vitamin D analogs, either by themselves or in combination with phototherapy or systemic agents (such as methotrexate, cyclosporine A, Humira®, Stelara®, Soriatane®, etc.), have been used for therapy. However, these agents can be extremely expensive, costing more than $20,000 per year per patient.

Histamine is a compound involved in local immune responses of humans and other animals. As part of an immune response to foreign pathogens, histamine is produced by basophils and mast cells found in nearby connective tissues. Upon release from these cells, histamines produce increased vascular permeability, causing fluid to escape from capillaries into tissues, which can lead to inflammation and itchiness among other responses. Histamine triggers an immune system response by combining with specific cellular histamine receptors. The four histamine receptors that have been discovered in humans and animals are designated $H_1$ through $H_4$. Compounds, known as antihistamines, have been developed that do not prevent the release of histamine but instead inhibit the action of histamine by blocking it from attaching to the histamine receptors. Most commonly used antihistamines inhibit action specifically at the $H_1$ receptor and are referred to as $H_1$ antihistamines. While some $H_1$ antihistamines have sedative side effects, so-called "second generation" or "non-sedating" antihistamines do not cross the blood-brain barrier and, thus, do not cause drowsiness. Further, not all $H_1$ antihistamines inhibit the inflammatory response that results from the release of histamine in humans.

Zemtsov is credited with discovering and confirming the presence of the phosphocreatine molecule ("Pcr") in human skin. Pcr has been found in both skin and internal organs, like skeletal muscle, and is an important energy storage molecule. Pcr assists in regenerating adenosine triphosphate ("ATP") molecules during periods of high metabolic demand, or ischemia. In turn, ATP molecules produce the energy required for all cellular functions. Topical application of Pcr can "recharge" skin cells. However, Pcr is a very unstable molecule. Nonetheless, Pcr can be regenerated by skin cells by topically applying a mixture of creatine and creatinine, denoted as "Cr/Crt." Topical mixtures of Cr/Crt have been used for the treatment and prevention of wrinkles and similar cosmetic applications. However, Cr/Crt has not previously been used in medical applications.

Extensive investments of time and capital are required to obtain Federal Drug Administration (FDA) approval to sell and market a new drug. The cost of approval is one reason that only three topical dermatological drugs were approved by the FDA in the last five years. Instead, pharmaceutical companies are primarily directing their efforts to develop and patent new delivery systems and formulations to more efficiently carry active ingredients (i.e., drugs) through the stratum corneum skin barrier. These new formulations include solid lipid nanoparticles, liposomes and niosomes, transferosomes, ethosomes, cyclodextrins, and sol-gel microcapsules.

Accordingly, there is a need for an anti-inflammatory, antipruritic, and moisturizing topical formulation for treating and promoting the healing of wounds and inflammatory conditions of the skin.

BRIEF SUMMARY

According to one aspect of the present invention, a formulation for the treatment of wounds and inflammatory skin conditions of the skin is disclosed. In at least one embodiment, a topically administrable composition for treating wounds and inflammatory conditions of the skin in mammals includes a therapeutic amount of antihistamine selected from the group consisting of a non-sedating antihistamine, a physiologically acceptable acid of a non-sedating antihistamine, a salt of a non-sedating antihistamine, an amide of a non-sedating antihistamine, and a combination of two or more thereof; a therapeutic amount of creatine; a therapeutic amount of creatinine; and emu oil product selected from the group consisting of emu oil, a biologically active fraction of emu oil, and a combination thereof.

In at least one embodiment, the non-sedating antihistamine is selected from the group consisting of cetirizine, levocetirizine, loratadine, fexofenadine, rupatadine, acrivastine, ebastine, bilastine, and a combination of two or more thereof. The physiologically acceptable acid of the non-sedating antihistamine is selected from the group consisting of an acid of cetirizine, an acid of levocetirizine, an acid of loratadine, an acid of fexofenadine, an acid of rupatadine, an acid of acrivastine, an acid of ebastine, an acid of bilastine, and a combination of two or more thereof. The salt of the non-sedating antihistamine is selected from the group consisting of a salt of cetirizine, a salt of levocetirizine, a salt of loratadine, a salt of fexofenadine, a salt of rupatadine, a salt of acrivastine, a salt of ebastine, a salt of bilastine, and a combination of two or more thereof. The amide of a non-sedating antihistamine is selected from the group consisting of an amide of cetirizine, an amide of levocetirizine, an amide of loratadine, an amide of fexofenadine, an amide of rupatadine, an amide of acrivastine, an amide of ebastine, an amide of bilastine, and a combination of two or more thereof.

In at least one embodiment, the composition includes 0.1 to 5.0 wt.-% of the antihistamine, 0.2-10.0 wt.-% creatine, 0.1-5.0 wt.-% creatinine, and at least 75 wt.-% of the emu oil product. In at least one embodiment, the composition includes 2.0 wt.-% of the antihistamine, 1.0 wt.-% creatine, 0.5 wt.-% creatinine, and at least 85 wt.-% of the emu oil product. In at least one embodiment, the composition further includes a preservative, and a neutral emulsifying agent. In at least one embodiment, the composition includes 0.1 to 1.0 wt.-% of preservative. In at least one embodiment, the composition includes 0.2 wt.-% of preservative. In at least one embodiment, the preservative is methylparaben, and the emulsifying agent is propylene glycol.

In at least one embodiment, the antihistamine is selected from the group consisting of cetirizine, a physiologically acceptable acid of cetirizine, a salt of cetirizine, an amide of cetirizine, and a combination of two or more thereof. In at least one embodiment, the antihistamine is selected from the group consisting of levocetirizine, a physiologically acceptable acid of levocetirizine, a salt of levocetirizine, an amide of levocetirizine, and a combination of two or more thereof.

According to one aspect of the present invention, a method of treating wounds and inflammatory conditions of the skin in mammals includes topically applying to the skin of a mammal a topically administrable composition that includes a therapeutic amount of antihistamine selected from the group consisting of a non-sedating antihistamine, a physiologically acceptable acid of a non-sedating antihistamine, a salt of a non-sedating antihistamine, an amide of a non-sedating antihistamine, and a combination of two or more thereof, a therapeutic amount of creatine, a therapeutic amount of creatinine, and emu oil product selected from the group consisting of emu oil, a biologically active fraction of emu oil, and a combination thereof; and repeating the topical application of the composition as indicated for resolution or control of the skin wound.

In at least one embodiment, the method includes a non-sedating antihistamine is selected from the group consisting of cetirizine, levocetirizine, loratadine, fexofenadine, rupatadine, acrivastine, ebastine, bilastine, and a combination of two or more thereof. In at least one embodiment, the method includes a physiologically acceptable acid of the non-sedating antihistamine is selected from the group consisting of an acid of cetirizine, an acid of levocetirizine, an acid of loratadine, an acid of fexofenadine, an acid of rupatadine, an acid of acrivastine, an acid of ebastine, an acid of bilastine, and a combination of two or more thereof. In at least one embodiment, the method includes a salt of the non-sedating antihistamine is selected from the group consisting of a salt of cetirizine, a salt of levocetirizine, a salt of loratadine, a salt of fexofenadine, a salt of rupatadine, a salt of acrivastine, a salt of ebastine, a salt of bilastine, and a combination of two or more thereof. In at least one embodiment, the method includes an amide of a non-sedating antihistamine is selected from the group consisting of an amide of cetirizine, an amide of levocetirizine, an amide of loratadine, an amide of fexofenadine, an amide of rupatadine, an amide of acrivastine, an amide of ebastine, an amide of bilastine, and a combination of two or more thereof.

In at least one embodiment, the composition of the method includes 0.1 to 5.0 wt.-% of the antihistamine, 0.2-10.0 wt.-% creatine, 0.1-5.0 wt.-% creatinine, and at least 75 wt.-% of the emu oil product. In at least one embodiment, the composition of the method includes 2.0 wt.-% of the antihistamine, 1.0 wt.-% creatine, 0.5 wt.-% creatinine, and at least 85 wt.-% of the emu oil product. In at least one embodiment, the composition of the method includes an antihistamine selected from the group consisting of cetirizine, a physiologically acceptable acid of cetirizine, a salt of cetirizine, an amide of cetirizine, and a combination of two or more thereof. In at least one embodiment, the composition of the method includes an antihistamine selected from the group consisting of levocetirizine, a physiologically acceptable acid of levocetirizine, a salt of levocetirizine, an amide of levocetirizine, and a combination of two or more thereof.

BRIEF DESCRIPTION OF THE DRAWINGS

FIG. 1 shows a method of treating wounds of the skin according to the present disclosure.

DETAILED DESCRIPTION

The present application discloses various formulations and methods for using the same for the treatment of wounds and inflammatory conditions of the skin in mammals. According to one aspect of the present disclosure, a formulation for the treatment and promotion of healing of wounds of the skin is disclosed. For the purposes of promoting an understanding of the principles of the present disclosure, reference will now be made to various embodiments and specific language will be used to describe the same. It will nevertheless be understood that no limitation of the scope of this disclosure is thereby intended, such alterations, modifications, and further applications of the principles of the disclosure being contemplated as would normally occur to one skilled in the art to which the disclosure relates.

A number of explanations and clinical trials are provided by way of explanation and not limitation. No theory of how the disclosure operates is to be considered limiting, whether proffered by virtue of description, comparison, or example. For the purposes of this disclosure, the term "emu oil" refers to lipid compositions, oils, and preparations of oils derived from the emu.

Emu oil, extracted or rendered from the body fat of the emu bird, has a number of beneficial properties for the treatment of wounds and inflammatory conditions of the skin. The beneficial properties of emu oil include that emu oil is noncomedogenic, antibacterial, moisturizing, anti-inflammatory, emulsifying, enhances transdermal penetration, and has a low potential for skin irritation. Taking each of these beneficial properties in turn, emu oil is noncomedogenic, meaning emu oil will not clog skin pores. Other such oils tend to clog pores in skin, which can result in the development of acne. Such oils include synthetic oils, like mineral oils, or animal oils, like mink or lard. Moreover, emu oil has been demonstrated to be antibacterial and moisturizing to skin. Bacterial secondary colonization and infection play important roles in the pathogenesis of atopic dermatitis, and the antibacterial properties of emu oil address this contributing factor. Further, moisturizers by themselves are therapeutic agents in the treatment of patients with psoriasis, atopic dermatitis, and other forms of eczema because moisturizers can improve skin hydration and normalize keratinocyte differentiation.

Emu oil has excellent skin barrier penetrating features and can enhance the transdermal penetration of active compounds, compounds otherwise unable to effectively treat disease beyond the epidermis. Emu oil is known to contain triglyceride esters of long-chain saturated and unsaturated fatty acids, including oleic acid, linoleic acid, palmitic acid, and stearic acid. Table 1 contains the typical chemical composition of emu oil which, being almost entirely triglyceride in nature, is a nearly completely neutral lipid. The transdermal penetration properties of emu oil are generally attributable to oleic acid, which enables penetration by fluidizing the intercellular lipids of the stratum corneum. However, studies of various long-chain fatty acids, including oleic acid, used as penetration enhancers have not reported a synergistic effect of using this particular property of emu oil with other active compounds as described herein.

Two other valuable properties of emu oil for a topical treatment delivery system are its emulsifying properties and low potential for irritation. Such emulsifying properties, absent the potential for irritation, enable emu oil to serve as both a carrier and an active compound in a formulation. In addition to the beneficial properties mentioned above, emu oil has anti-inflammatory properties. For example, topically administered emu oil has been shown to be as effective as orally administered, high-dose ibuprofen. Research suggests that at least some of emu oil's anti-inflammatory properties are due to TNF-alpha inhibition, which is a key target inflammatory molecule in systemic psoriasis therapy. Examples of prescription treatments for systemic psoriasis that operate by inhibiting TNF-alpha include Enbrel® and Humira®. However, prior to the present disclosure, no topical formulation with TNF-alpha inhibitory effects has been used to treat inflammatory or any other disease of the skin. Therefore, emu oil may act as a therapeutic agent for some skin conditions independent of any other active compound.

Certain of the beneficial properties of emu oil are most effective in treating specific types of skin conditions and less effective on others. Nonetheless, by combining emu oil with additional active compounds, the beneficial properties of emu oil may potentiate the therapeutic effects of both the emu oil and the additional active compounds. Accordingly, in at least one embodiment of the present disclosure, emu oil may be included in a formulation to dissolve one or more additional active compounds, carry the one or more additional active compounds through the skin barrier, and provide one or more therapeutic effects that are synergistically enhanced by the combination with the one or more additional active compounds.

In at least one embodiment according to the present disclosure, emu oil may be combined with a non-sedating antihistamine compound to treat wounds and inflammatory conditions of the skin such as psoriasis and atopic dermatitis. One non-limiting example of a non-sedating antihistamine is cetirizine. Cetirizine is commonly used orally to treat hay fever, urticaria (i.e., hives), angioedema, and allergies. In addition to antiallergic, bronchodilatory, and antispasmodic properties, cetirizine has numerous pharmacological effects that are highly useful for the treatment of wounds and inflammatory conditions of the skin if used as a topical agent.

As a potent second-generation antihistamine, cetirizine has antipruritic properties that are very beneficial in treating wounds and inflammatory skin conditions, particularly atopic dermatitis, which has been described as a vicious cycle of itch-scratch-itch. In addition to relieving the symptoms of itch, antipruritic antihistamines help to prevent progression of the condition by suppressing the scratching impulse (i.e., the so-called Koebner phenomenon). Moreover, as a second-generation, non-sedating antihistamine, cetirizine has an excellent safety profile, which enables cetirizine (marketed as Zyrtec®) to be sold over-the-counter without a prescription. Further, cetirizine and its related isomers are unique among non-sedating antihistamines in that each has various anti-inflammatory properties useful for the treatment of inflammatory skin disease. Namely, cetirizine inhibits expression of adhesion molecules in patients with both atopic dermatitis and psoriasis and inhibits both T lymphocytes and monocytes, which play a central role in the pathogenesis of atopic dermatitis and psoriasis. Finally, cetirizine exerts anti-inflammatory effects on neutrophils apart from $H_1$ antagonism and inhibits eosinophil-related skin inflammation.

The anti-inflammatory properties of cetirizine are distinct from its other $H_1$ antihistamine features. For example, diphenhydramine (marketed as Benadryl®) is specifically contraindicated to treat inflammatory skin disease, such as eczema and psoriasis. In fact, where sold in the United States, the packaging for diphenhydramine includes a warning label clearly stating that it should not be used on "raw or broken skin" or "areas producing discharge." Other commonly used non-sedating antihistamines that do not have anti-inflammatory properties include loratadine (marketed as Claritin®) and fexofenadine (marketed as Allegra®). Therefore, not all non-sedating, $H_1$ antihistamines are appropriate for the treatment of inflammatory skin conditions.

Though emu oil and cetirizine both have anti-inflammatory properties, each utilizes completely different biochemical pathways. Consequently, instead of enabling merely additive beneficial anti-inflammatory effects, the combination of emu oil and cetirizine provides a synergistic enhancement of the beneficial effects of both active compounds in treating inflammatory skin conditions. Furthermore, emu oil, in addition to being a therapeutic agent, also enables penetration of cetirizine into the skin, thereby improving the efficacy of cetirizine separate from the synergistic effect.

Cetirizine is a racemic 50/50 mixture of levocetirizine, which is the active enantiomer (or L-stereoisomer), and the much less biologically active enantiomer (or D-stereoisomer). Like cetirizine, levocetirizine is a non-sedating antihistamine that includes anti-inflammatory properties. Accordingly, in at least one embodiment of the present disclosure, emu oil may be combined with levocetirizine to treat wounds and inflammatory conditions of the skin such as psoriasis and atopic dermatitis. Other non-sedating, anti-inflammatory antihistamines include, but are not limited to rupatadine, acrivastine, ebastine and bilastine.

Wound healing after any type of injury to the skin is an extremely complex, multistage process characterized by inflammation and new tissue formation and remodeling, which are both processes that require great amounts of cellular energy. Excessive inflammation and bacterial infection can delay wound healing and cause further scaring. Moreover, serious skin infections can become systemic and life threatening, for example, as with sepsis. Many wound healing creams, such as Neosporin® or Polysporin®, contain antibacterial medicines. However, dermatologists prescribe these wound healing creams infrequently because of high prevalence of contact dermatitis, or "poison ivy-type" allergic reactions, associated with the use of such treatments. Further, most healing wounds show signs of pruritus, and the resulting scratching can delay wound healing.

In at least one embodiment of the present disclosure, emu oil may be combined with a mixture of creatine and creatinine, denoted as "Cr/Crt," to treat and promote the healing of wounds of the skin, as well as inflammatory skin conditions such as psoriasis and atopic dermatitis. As disclosed herein, the application of Cr/Crt results in the regeneration of phosphocreatine molecules ("Pcr") in mammalian skin. Because Pcr assists in regenerating ATP molecules, which produce energy in skin and other cells, topical application of Pcr via the application of Cr/Crt can provide skin cells with the energy needed to heal wounds. Further, the epidermal transport properties of emu oil facilitate penetration of Cr/Crt through the skin barrier, which is particularly effective in treating partially healed wounds.

The combination of emu oil and Cr/Crt in one topical formulation enables these active compounds to synergistically aid the healing of wounds and inflammatory conditions of the skin. In addition to facilitating penetration of Cr/Crt through the skin barrier, emu oil also promotes wound healing by reducing excessive inflammation, which can interfere with wound healing and induce excessive scaring of a wound. Moreover, the antibacterial properties of emu oil promote wound healing by reducing the incidence of secondary infection, which can further interfere with the healing process. Previous studies have shown that emu oil alone can decrease wound healing time and decrease scar formation in burn victims based on the results of a double-blind study. Therefore, by combining emu oil and Cr/Crt in one treatment, the formulation may promote and facilitate the healing process of skin wounds by providing cellular energy to drive the healing process while concurrently reducing inflammation and the incidence of bacterial infection.

In at least one embodiment of the present disclosure, emu oil may be combined with Cr/Crt and a non-sedating antihistamine to treat skin wounds and promote the healing process of skin wounds, as well as inflammatory skin conditions. As disclosed herein, non-sedating antihistamines, such as cetirizine, have anti-inflammatory and antipruritic properties that operate through different biochemical pathways from emu oil. These properties can be advantageous in promoting the healing process of skin wounds. Most healing skin wounds show signs of pruritus, and the resulting scratching can delay wound healing. Accordingly, the antipruritic properties of cetirizine are of value in the healing process. Further, the anti-inflammatory properties of certain non-sedating antihistamines, such as cetirizine, can promote wound healing by reducing excessive inflammation that can interfere with wound healing and induce excessive scaring of a wound. As disclosed herein, the combination of a non-sedating antihistamine, Cr/Crt, and emu oil has now been shown to synergistically potentiate the effects of these active compounds to accelerate the wound healing process. Consequently, a formulation combining emu oil, Cr/Crt, and a non-sedating antihistamine has been demonstrated to facilitate the wound healing process by addressing key aspects of the healing process via different biochemical pathways. The use of natural energy supplementation, for example with the topical use of Cr/Crt, in combination with anti-inflammatory compounds to facilitate the healing process in mammalian skin has not been disclosed previously.

In at least one embodiment according to the present disclosure, a formulation 10 may contain by weight 75-100% emu oil, 0.1-5.0% non-sedating antihistamine, a Cr/Crt mixture of 0.2-10.0% creatine and 0.1-5.0% creatinine, and 0.1-1.0% preservative, with the balance being a neutral emulsifying solvent. In at least one embodiment, the formulation 10 may contain by weight 75-100% emu oil, 0.1-5.0% cetirizine, a Cr/Crt mixture of 0.2-10.0% creatine and 0.1-5.0% creatinine, 0.1-1.0% methylparaben preservative, and the balance propylene glycol or other neutral emulsifying solvent. In at least one embodiment, the formulation 10 may contain by weight at least 85% emu oil, 2.0% cetirizine, a Cr/Crt mixture of 1% creatine and 0.5% creatinine, 0.2% methylparaben preservative, and the balance propylene glycol. In at least one embodiment, the formulation 10 may contain by weight 75-100% emu oil, 0.1-5.0% levocetirizine, a Cr/Crt mixture of 0.2-10.0% creatine and 0.1-5.0% creatinine, 0.1-1.0% methylparaben preservative, and the balance propylene glycol or other neutral emulsifying solvent. In at least one embodiment, the formulation 10 may contain by weight at least 85% emu oil, 2.0% levocetirizine, a Cr/Crt mixture of 1% creatine and 0.5% creatinine, 0.2% methylparaben preservative, and the balance propylene glycol.

In one aspect of the present disclosure, the formulations disclosed herein may be used in a method 100 of treating wounds and inflammatory conditions of the skin as shown in FIG. 1. The method 100 may include a step 110 of applying the formulation 10 to an affected area of skin. The method 100 may further include a step 120 of periodically repeating application of the formulation 10 to the affected area of skin until the wound is healed or the inflammatory condition is resolved or controlled.

The efficacy of combining emu oil with non-sedating antihistamine and with Cr/Crt was determined by the following experiment. The following experiment is illustrative, but not limiting, of the methods and compositions of the present disclosure. Other suitable modifications and adaptations of the variety of conditions and parameters normally encountered in clinical therapy and obvious to those skilled in the art, having the benefit of this disclosure, are within the scope of the present disclosure.

Experiment

In order to determine the efficacy of combining emu oil, a non-sedating antihistamine, and Cr/Crt as active compounds for the promotion of wound healing and the treatment of inflammatory skin conditions, a single-blind clinical study was conducted. The study was designed to determine: (i) the efficacy of the active compounds in promoting the healing process of skin wounds; (ii) whether the active compounds worked synergistically or simply provided additive effects; and (iii) the relative quantifiable effectiveness of each of the active compounds. Because of very stringent inclusion criteria, only five patients were enrolled and completed the study. As a single-blind study, the five research subjects received five tubes of preparations in cream form, labeled as A, B, C, D, and E, without knowledge of the formulations therein. However, a principal investigator and a study coordinator knew and recorded the formulations contained in each tube. Regarding the active compounds included in the study, Cream A included Cr/Crt and cetirizine in an emu oil base, Cream C included only emu oil, Cream D included Cr/Crt in an emu oil base, and Cream E included cetirizine in an emu oil base. Cream B, which contained no active compounds, included only propylene glycol base and served as a placebo. Cream B was used as a control preparation to provide a reference point for the degree of improvement observed for the other trial preparations. Each cream included an identical amount of Cr/Crt, namely 1.5% by weight, which included 1.0% creatine and 0.5% creatinine by weight. Further, each cream included methylparaben as a preservative and varying amounts of propylene glycol as a neutral emulsifying solvent. The study was conducted for 15 days.

Subjects selected for the study had at least five different wounds on different areas of their body. The causes of the wounds included in the study included skin cancer treatment sites, shave or burn removal of warts, and skin biopsy sites. Accordingly, each research subject applied each of the trial creams to a different wound site on the subject's body selected at random by the subject. Each trail cream was applied on one wound only. Consequently, each research subject was his/her own positive and negative control. Further, though each wound was somewhat different and located in different anatomical areas from one another, the random selection of the treatment site by the subject for a given trial cream ensured statistical independence in the design of the study.

At the end of the study, each research subject completed a questionnaire specifically asking "which of the five creams worked the best" and asking the subject to numerically rate the efficacy of each cream on a scale of 0 (not effective) to 10 (extremely effective). The subjects' ratings were then multiplied by a factor of ten to enable simple percentage point comparisons between the trial creams. Moreover, each subject was asked to report any systemic or dermatological side effects of the creams, such as irritation, stinging, or pruritus. The subjects were asked to rank the trial cream that produced the fastest healing with least side effects as a "10." After the subjects ranked the cream that worked the best, each subject was told that cream B was a placebo and was asked to rate creams C, D, and E in comparison to cream B. Because scar tissue requires 6-12 months to completely form and because each wound was a different and in different anatomical area, the study could not include a determination of which cream produced best cosmetic results. Instead, the evaluations of the subjects' wounds addressed which trial cream produced the fastest healing with minimal subjective and objective side effects. Theoretically, the fastest acting treatment will translate into best cosmetic results.

Furthermore, the clinical response of each subject was assessed by the principal investigator, a physician trained, experienced, and Board Certified in dermatology, at the end of the 15-day study by comparing the condition of the subjects' wounds to a pre-trial evaluation on 0 to 10 scale similar to that at used by the subjects, where "10" indicated the cream that produced the fastest healing with least side effects, "5" indicated that wound healing was 50% better than the placebo, and zero indicted that wound healing was no better than the placebo. The physician compared the rate of healing and subjective side effects, such as pain, itching and burning, of creams A, C, D, and E in comparison to the placebo, Cream B. Similarly, the physician's evaluations were then multiplied by a factor of ten to enable simple percentage point comparisons between the trial creams. Finally, the study coordinator obtained clinical photographs of all areas treated at the beginning and end of the study.

The research subjects did not use any other prescription medication or over-the-counter topical preparation during the duration of the study. Informed written consent was obtained prior to initiation of the study from each research subject. No financial compensation was provided to any of the research subjects; however, each received a complimentary office visit and free medication. Further, at the end of the study, the subjects were offered and received a free complimentary tube of the cream of their choice (either cream A, B, C, D, or E).

Table 2 presents the physician's evaluations of the improvement or worsening of the research subjects' skin conditions by the end of the study, relative to the beginning of the study and the control Cream B, for each of the trial creams A, C, D, and E. As shown Table 2, Cream A was rated most effective because it demonstrated the greatest improvement compared to creams B, C, D, and E, as reflected in the mean evaluation ratings across all subjects. Statistical analysis determined that the demonstrated improved effect of Cream A over the other creams was statistically significant (i.e., $p<0.05$). Further, Cream A had no reported side effects.

Table 2 includes a column of data for the "Additive Effect of Creams C, D, and E" calculated for each subject based upon the physician's evaluation. The calculated additive effect of Cream C, Cream D, and Cream E was determined by, first, subtracting the rated effect of Cream B (the control) from the ratings given to Cream C, Cream D, and Cream E, which results in a value representing the beneficial effect of each cream in addition to the effect provided by Cream B. The resulting additional effects were then added together. Essentially, the calculated additive effect quantifies the combined effects of Cream C, Cream D, and Cream E, beyond the effect of the control cream, attributable to the active compounds operating separately. Thus, the calculated additive effect represents the expected or anticipated effect of combining and administering the three active compounds, Cr/Crt, cetirizine, and emu oil. On the other hand, the extent to which the rated effect of Cream A exceeds the calculated additive effect of Cream C, Cream D, and Cream E represents the unexpected and synergistic effect of combining and administering the three active compounds together. The synergistic effect may be calculated by subtracting the calculated additive effect of Cream C, Cream D, and Cream E from the rated evaluations for Cream A. Accordingly, Table 2 further includes the resulting unexpected and synergistic effect for each subject under column heading, "Synergistic Effect of Cream A," which contains the calculated percentage point improvement of Cream A produced by the synergistic effect of Cream A beyond the simple additive effects of the active compounds administered separately via Cream C, Cream D, and Cream E.

As shown in Table 2, Cream A was on average 50% more effective than the net effects of Cream C, Cream D, and Cream E taken separately. Further, the synergistic effect was statistically significant. Because the ratings given to Cream A were statistically greater than the calculated additive effect of Cream C, Cream D, and Cream E, one may conclude that the combined effect of the active compounds included in Cream A exceeded the expected effect of these compounds acting separately by 50% on average. Therefore, the study unequivocally demonstrated that Cr/Crt, cetirizine, and emu oil synergistically potentiate each other's beneficial effects and that the synergistic effect was statistically significant.

The data of Table 2 further demonstrates that, while treatment with emu oil alone (Cream C) produced some benefits, the combination of Cr/Crt and emu oil (Cream D) has statistically significant beneficial effects for wound healing. One reason for including a placebo without an active compound in the study was to distinguish whether an active compound, and in particular Cr/Crt, might have a negative impact on wound healing. To the contrary, as the results for Cream D indicate, Cr/Crt combined with emu oil demonstrated a statistically significant improvement in wound healing.

Table 3 presents the research subjects' ratings of their own skin conditions at the end of the study, relative to the beginning of the study, for each of the trial creams A, B, C, and D. As shown in Table 3, the subjects' ratings generally corroborated the physician's evaluations. For example, most of the research subjects rated Cream A as the most effective for the treatment of his/her wound to a statistically significant degree. One subject rated Cream D (Cr/Crt and emu oil) as most effective. Unlike Cream A, which demonstrated statistically significant improvement in comparison to the placebo (Cream B), creams C, D, and E did not achieve statistically significant improvement in comparison to Cream B.

As shown in Table 3, Cream A was demonstrated to be 88% more effective than Cream B (the control) to a statistically significant degree as rated by the research subjects. In addition, Cream A was on average 24% more effective than the net effects of Cream C, Cream D, and Cream E taken separately, thereby demonstrating the same synergistic effect proven with the physician's evaluations, but as rated by the subjects. However, due to the small sample size, the synergistic effect based on the subjects' ratings was highly suggestive but not statistically significant (i.e., 0.10>p>0.05). In addition, the subjects' ratings similarly corroborated the physician's evaluations indicating a statistically significant improvement in wound healing using Cr/Crt in combination with emu oil. None of the research subjects reported any systemic side effects from any of the creams A, B, C, D, or E.

In summary, the clinical study as a whole clearly demonstrated that cetirizine, emu oil, and Cr/Crt synergistically potentiated each other's beneficial effects to promote the healing process for wounds of the skin and other inflammatory skin conditions utilizing completely different biochemical pathways.

While various embodiments of a formulation for the treatment of wounds and inflammatory skin conditions of the skin and methods for using the same have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible and are therefore contemplated by the inventor. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

TABLE 1

Typical Emu Oil Fatty Acid Composition

| Fatty Acid | Percentage by Weight |
|---|---|
| Myristic | 0.4% |
| Palmitic | 21.5% |
| Palmitoleic | 3.7% |
| Stearic | 10.6% |
| Oleic | 51.4% |
| Linoleic | 12.7% |
| Linolenic | 0.9% |

TABLE 2

Physician Evaluations of Trial Creams

| Subject | Cream A | Cream B (Control) | Cream C | Cream D | Cream E | Additive Effect of Creams C, D and E | Synergistic Effect of Cream A (%) |
|---|---|---|---|---|---|---|---|
| 1 | 100 | — | 10 | 20 | 0 | 30 | 70 |
| 2 | 100 | — | 10 | 30 | 10 | 50 | 50 |
| 3 | 100 | — | 10 | 30 | 30 | 70 | 30 |
| 4 | 100 | — | 10 | 20 | 30 | 50 | 50 |
| 5 | 100 | — | 10 | 20 | 10 | 50 | 50 |
| Mean | 100 | — | 10 | 24 | 16 | 50 | 50 |

TABLE 3

Patient Ratings of Trial Creams

| Subject | Cream A | Cream B (Control) | Cream C | Cream D | Cream E | Additive Effect of Creams C, D and E | Synergistic Effect of Cream A (%) |
|---|---|---|---|---|---|---|---|
| 1 | 100 | — | 20 | 20 | 10 | 50 | 50 |
| 2 | 40 | — | 20 | 100 | 0 | 120 | −80 |
| 3 | 100 | — | 10 | 30 | 20 | 50 | 50 |
| 4 | 100 | — | 10 | 20 | 30 | 60 | 40 |
| 5 | 100 | — | 20 | 20 | 0 | 40 | 60 |
| Mean | 88 | — | 16 | 38 | 12 | 64 | 24 |

The invention claimed is:

1. A topically administrable composition for treating skin wounds in mammals, the composition comprising:
   1.0% to 3.0% wt.-% cetirizine;
   a therapeutic amount of creatine;
   a therapeutic amount of creatinine; and
   80% to 90% wt.-% of emu oil;

wherein the composition comprises 1.5 wt.-% of the therapeutic amount of creatine and the therapeutic amount of creatinine in combination.

2. The composition of claim 1, wherein the composition comprises:
   2.0 wt.-% of the cetirizine; and
   85% to 90% wt.-% of the emu oil.

3. The composition of claim 1, wherein the composition further comprises:
   a preservative; and
   a neutral emulsifying agent.

4. The composition of claim 3, wherein the preservative comprises methylparaben, and the emulsifying agent comprises propylene glycol.

5. A method of treating skin wounds, the method comprising:
   topically applying to the skin of a mammal a topically administrable composition comprising:
     1.0% to 3.0% wt.-% of cetirizine,
     a therapeutic amount of creatine,
     a therapeutic amount of creatinine, and
     80% to 90% wt.-% of emu oil;
   wherein the composition comprises 1.5 wt.-% of the therapeutic amount of creatine and the therapeutic amount of creatinine in combination; and
   repeating the topical application of the composition as indicated for resolution or control of the skin wound.

6. The method of claim 5, wherein the composition comprises:
   2.0 wt.-% of the cetirizine; and
   85% to 90% wt.-% of the emu oil.

7. A topically administrable composition for treating skin wounds in mammals, the composition comprising:
   1.0% to 3.0% wt.-% of cetirizine;
   a therapeutic amount of creatine;
   a therapeutic amount of creatinine;
   80% to 90% wt.-% of emu oil;
   a preservative; and
   a neutral emulsifying agent comprising propylene glycol;
   wherein the composition comprises 1.5 wt.-% of the therapeutic amount of creatine and the therapeutic amount of creatinine in combination.

8. The composition of claim 7, wherein the composition comprises:
   2.0 wt.-% of the cetirizine; and
   85% to 90% wt.-% of the emu oil.

9. The composition of claim 7, wherein the preservative comprises methylparaben.

10. The composition of claim 1, wherein the preservative comprises methylparaben.

* * * * *